(12) United States Patent
O'Connell et al.

(10) Patent No.: US 9,917,994 B2
(45) Date of Patent: Mar. 13, 2018

(54) VISUAL AND TACTILE ASSESSMENT TOOL

(71) Applicant: Medtronic Vascular, Inc., Santa Rosa, CA (US)

(72) Inventors: Barry O'Connell, Ballybrit (IE); Brian Dowling, Ballybrit (IE); James Smedley, Ballybrit (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 130 days.

(21) Appl. No.: 14/940,211

(22) Filed: Nov. 13, 2015

(65) Prior Publication Data

US 2016/0139399 A1 May 19, 2016

Related U.S. Application Data

(60) Provisional application No. 62/079,332, filed on Nov. 13, 2014.

(51) Int. Cl.
| | | |
|---|---|---|
| *H04N 5/225* | (2006.01) | |
| *G02B 25/00* | (2006.01) | |
| *A61B 5/00* | (2006.01) | |
| *A61B 5/02* | (2006.01) | |
| *G06F 1/16* | (2006.01) | |
| *H04M 1/21* | (2006.01) | |
| *G02B 25/02* | (2006.01) | |

(52) U.S. Cl.
CPC .......... *H04N 5/2254* (2013.01); *A61B 5/7425* (2013.01); *G02B 25/002* (2013.01); *G02B 25/02* (2013.01); *G06F 1/1632* (2013.01); *H04M 1/21* (2013.01); *A61B 5/02007* (2013.01)

(58) Field of Classification Search
None
See application file for complete search history.

(56) References Cited

U.S. PATENT DOCUMENTS

| 8,681,437 B2 | 3/2014 | Jaffee |
|---|---|---|
| 9,007,522 B1 | 4/2015 | O'Neill et al. |
| | (Continued) | |

FOREIGN PATENT DOCUMENTS

| DE | 202012101167 U1 | 7/2013 |
|---|---|---|
| EP | 2500758 | 9/2012 |

OTHER PUBLICATIONS

Anonymous Universal Clip on Microscope Lens-60x Zoom LED Microscope for all Mobile Phones: Amazon in Electronics, May 23, 2014.

(Continued)

*Primary Examiner* — Mark T Monk

(57) ABSTRACT

A selectively attachable and removable visual and tactile assessment tool or clip for use with a mobile device is provided. Clip is an elongate member forming a curvilinear shape having a magnifying lens at a distal end thereof. Clip has a transparent tubular member disposed between first and second openings through the body portion of the clip. Tubular member has varying internal diameters to simulate, for example, the constriction or stenosis of a patient's vessel lumen. Once clip is attached to mobile device and the magnifying lens is positioned over the camera of the mobile device, a catheter is inserted through tubular member. The magnifying lens enlarges the size of the catheter displayed on the screen of the mobile device.

20 Claims, 10 Drawing Sheets

(56) References Cited

U.S. PATENT DOCUMENTS

| | | | |
|---|---|---|---|
| 2004/0212702 A1* | 10/2004 | Suh | G02B 7/10 |
| | | | 348/240.99 |
| 2009/0093274 A1 | 4/2009 | Yamamoto | |
| 2009/0181729 A1 | 7/2009 | Griffin et al. | |
| 2011/0188782 A1 | 8/2011 | Thompson et al. | |
| 2012/0157160 A1 | 6/2012 | Ozcan et al. | |
| 2012/0236425 A1* | 9/2012 | O'Neill | G02B 7/14 |
| | | | 359/827 |
| 2013/0157351 A1 | 6/2013 | Ozcan et al. | |
| 2014/0267882 A1 | 9/2014 | O'Neill et al. | |
| 2015/0003821 A1 | 1/2015 | Overall | |

OTHER PUBLICATIONS

International Search Report and Written Opinion from International Application No. PCT/US2015/060512, dated Mar. 17, 2016, 11 pp.
International Preliminary Report on Patentability from International Application No. PCT/US2015/060512, dated May 16, 2017, 8 pp.

\* cited by examiner

VISUAL AND TACTILE ASSESSMENT TOOL

RELATED APPLICATIONS

This application claims the benefit under 35 U.S.C. § 119 of U.S. Provisional Patent Application No. 62/079,332 filed on Nov. 13, 2014.

FIELD OF THE INVENTION

This invention relates generally to methods and devices for imaging with mobile devices (e.g., mobile telephones, mobile texting devices, personal media players, tablet devices, laptop computers, desktop computers, gaming devices, and/or devices capable of linking electronically to another device or to a network such as the Internet, etc.), and specifically to removable functional components for use with the image capturing capability of mobile devices.

BACKGROUND OF THE INVENTION

Digital Processing technology has made it possible for mobile devices to include cameras or other imaging devices that permit users to capture images or video. These images can be stored, processed, and transmitted. However, there are many design constraints with onboard cameras in mobile devices that can limit the weight, size, shape, adjustability, and magnification of the lensing systems of such cameras. Consequently, imaging devices in mobile devices are inadequate for a wide variety of imaging or analysis needs and may produce images which are hard to see with sufficient detail. There exists a need to provide an imaging analysis tool, such as a magnification system which removably mounts to a device, does not interfere with its normal operations, can be quickly enabled when magnification is needed and quickly removed when magnification is not needed. The magnification system must also not cover up or prevent the user from seeing the entire screen of the mobile device and also allow for touch-screen functionality.

BRIEF SUMMARY OF THE INVENTION

Embodiments hereof relate to a selectively attachable and removable visual and tactile assessment tool or clip for use with mobile device. Clip is an elongate member having an outer surface and an inner surface forming a curvilinear shape. The curvilinear shape of clip and selection of materials for first distal portion, second distal portion and body portion are such that retainer portion is variable to accommodate a plurality of sizes of mobile devices. In some embodiments, at least a portion first distal and second distal portions and body portion are made of a material (e.g., a polymer or a silicone) that is sufficiently elastic to permit a degree of bending or stretching in order to expand or widen retainer portion to accommodate different sizes of mobile devices. When clip is made of such a material, retainer portion may be temporarily widened while sliding clip onto mobile device, but at least body portion remains sufficiently stiff, rigid, or resilient to urge at least one of the first and second distal portions to return to its original position. In this manner, first and second distal portions exert a gripping force against a portion of mobile device.

Clip has a transparent tubular member disposed between first and second openings of body portion. Tubular member can have varying internal diameter sizes such as a first diameter, corresponding with first opening and a second diameter 68 corresponding with second opening. The varying internal diameter sizes of tubular member can simulate, for example, the constriction or stenosis of a patient's vessel lumen.

Once clip is attached to mobile device, an object, such as a balloon catheter, is inserted through first opening of body portion. An optical system on clip acts as a magnifying lens to enlarge the size of the catheter displayed on the screen of the mobile device. Catheter slides without restriction through first diameter of tubular member until catheter reaches second diameter of tubular member. At this point, the user must exert more pressure to advance catheter through second diameter and out second opening of body portion. During the advancement of catheter through tubular member, the video image received through onboard camera is displayed on screen.

Another embodiment hereof relates to selectively attachable and removable visual and tactile assessment tool or support member for use with mobile device. Support member has a receiving portion, an optical system disposed within receiving portion and an analysis portion. Optical system is recessed within receiving portion of support member, which allows mobile device to lay flat on a planar surface. Optical system is positioned adjacent to one side of support member in order to be in alignment with onboard camera which is located on rear face along top edge and adjacent a corner of rear face. Thus, optical system is disposed above and in visual communication with analysis portion in order to capture images or video of objects disposed within analysis portion.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. While the disclosure refers to illustrative embodiments for particular applications, it should be understood that the disclosure is not limited thereto. Modifications can be made to the embodiments described herein without departing from the scope of the present disclosure. Those skilled in the art with access to this disclosure will recognize additional modifications, applications, and embodiments within the scope of this disclosure and additional fields in which the disclosed examples could be applied. Therefore, the following detailed description is not meant to be limiting. Further, it is understood that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

References to "one embodiment," "an embodiment," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" and "distally" are positions distant from or in a direction away from the clinician. "Proximal" and "proximally" are positions near or in a direction toward the clinician.

Figure 1:
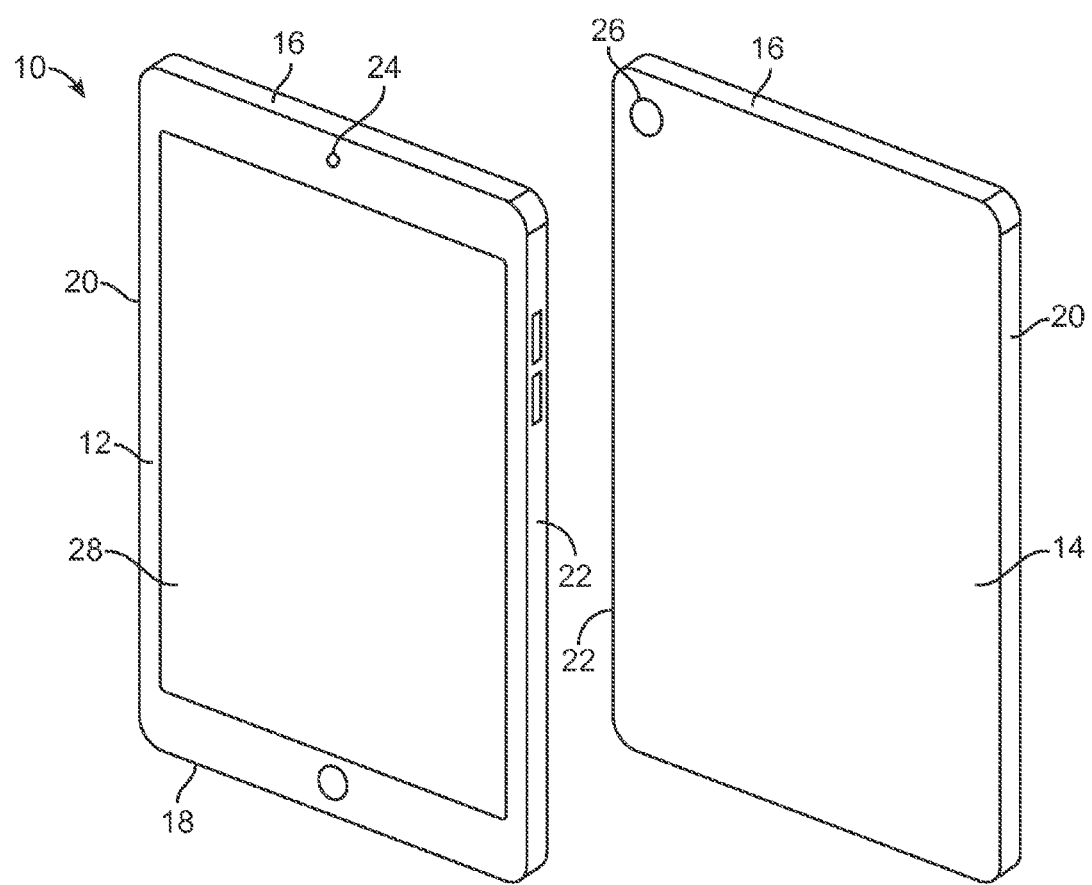
FIG. 1 is a front and rear view of an exemplary mobile device.

FIG. 1 illustrates two views of an example of a mobile device 10 with which a selectively attachable and removable visual and tactile assessment tool may be used. The mobile device 10 may be any electronic device configured to capture images, such as a mobile phone, media player, portable gaming device, tablet computer, or the like. For example, the mobile device 10 illustrated in FIG. 1A is a hand-held computing device sold under the trademark IPAD by Apple, Inc. of Cupertino, Calif. However, the present disclosure is not limited to any single type of mobile device.

The mobile device 10 may include two generally parallel, generally planar faces, such as a front face 12 and a rear face 14. The mobile device 10 may also have multiple edges such as a top edge 16, bottom edge 18, left edge 20 and right edge 22 (when viewing front face 12 of mobile device 10). As shown, mobile device 10 includes an onboard camera 24 that is centrally located on front face 12 of mobile device 10 in a central region adjacent top edge 16 that is positioned generally about the same distance from left and right edges 20, 22 of mobile device 10. In some embodiments, mobile device 10 may have another onboard camera 26 located on rear face 14 either along top edge 16 or adjacent a corner of rear face 14. Mobile device 10 has a screen 28 on front face 12 adjacent on board camera 24. Although specific example placements of onboard cameras 24 and 26 are shown and described, the examples are illustrative only, and are not intended to be limiting.

Figure 2:
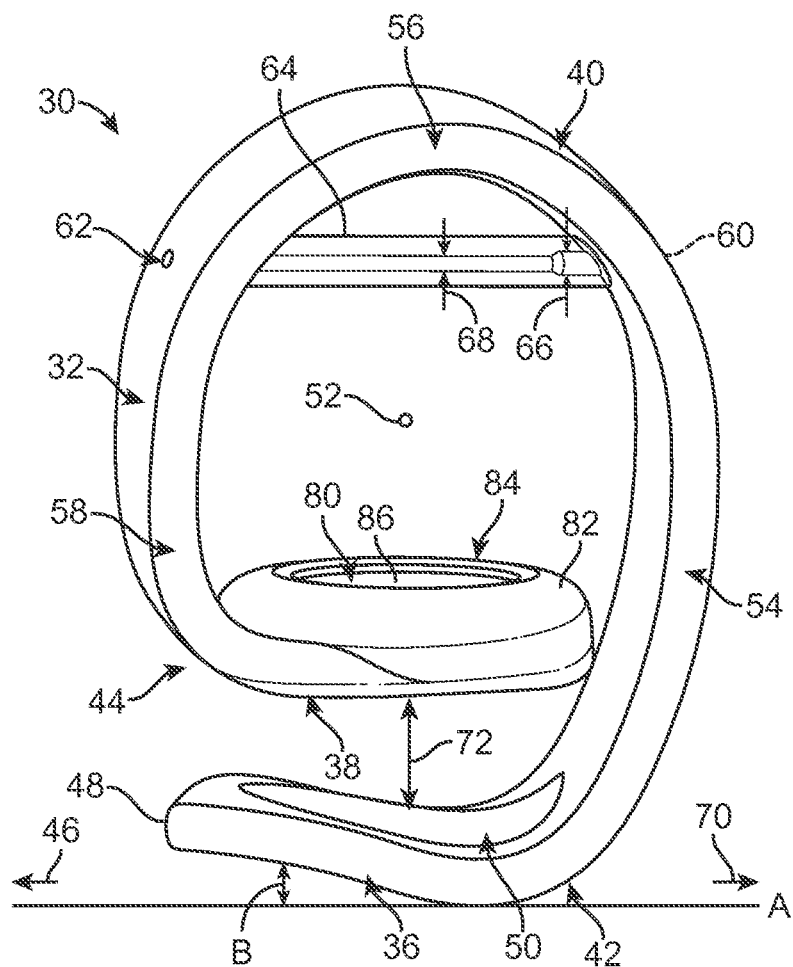
FIG. 2 is a side view of the assessment tool.
Figure 3:
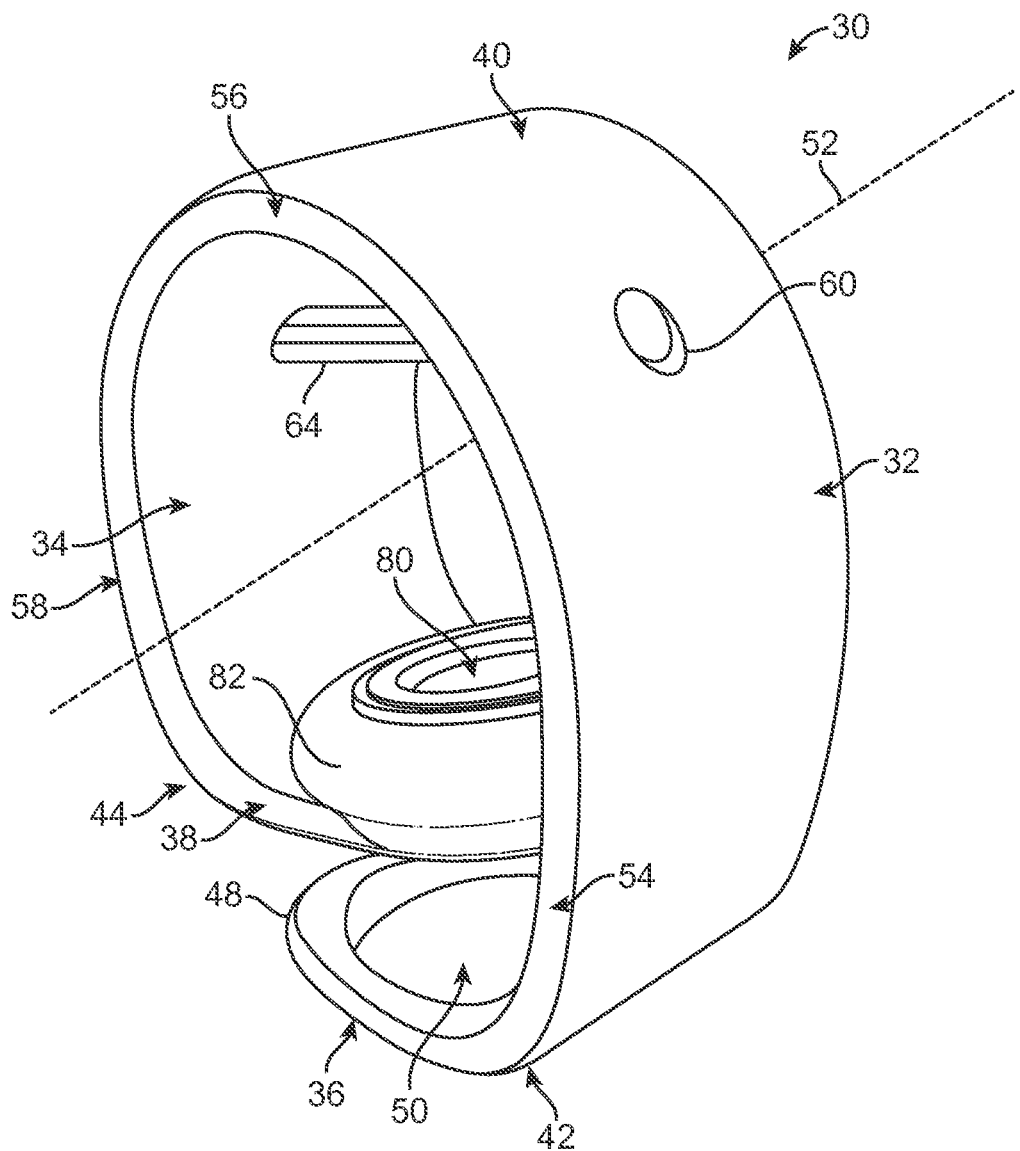
FIG. 3 is a perspective view of assessment tool.
Figure 4:
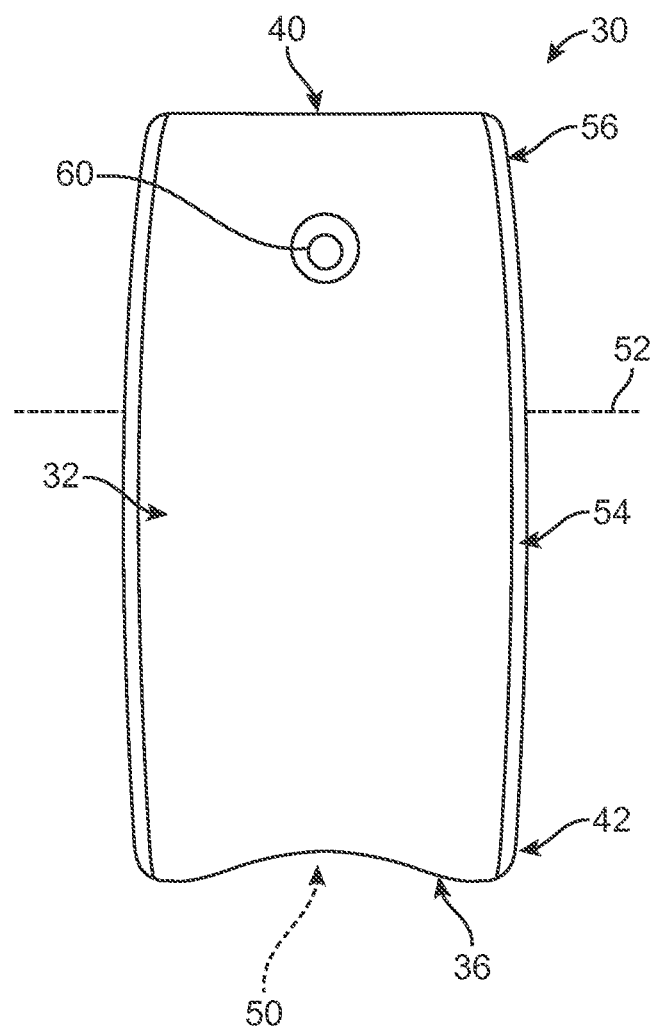
FIG. 4 is a side view of assessment tool.
Figure 5:
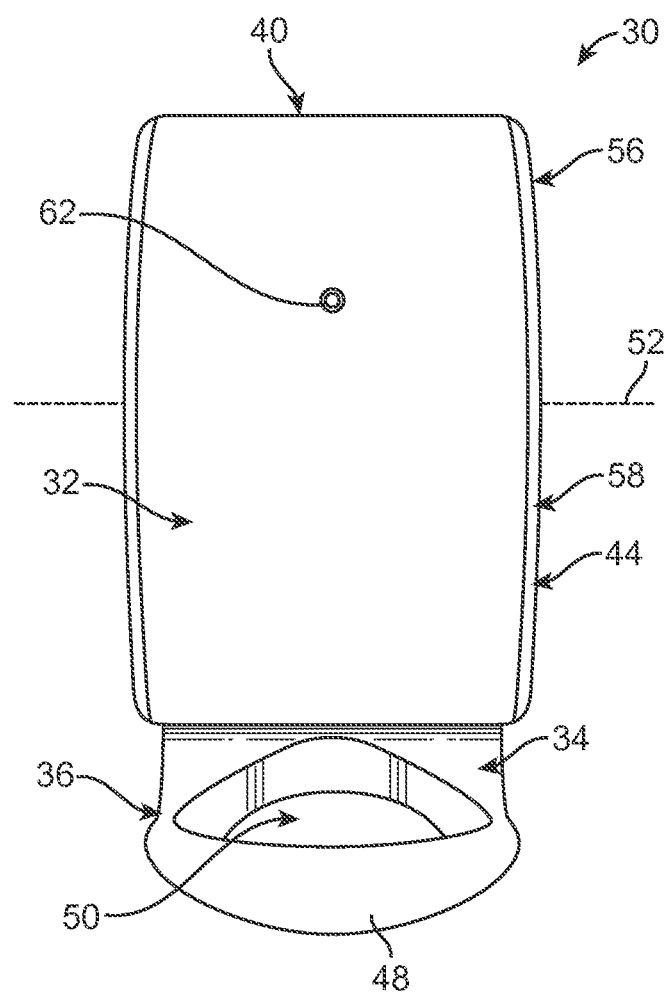
FIG. 5 is a side view (of an opposite side of FIG. 4) of assessment tool.
Figure 6:
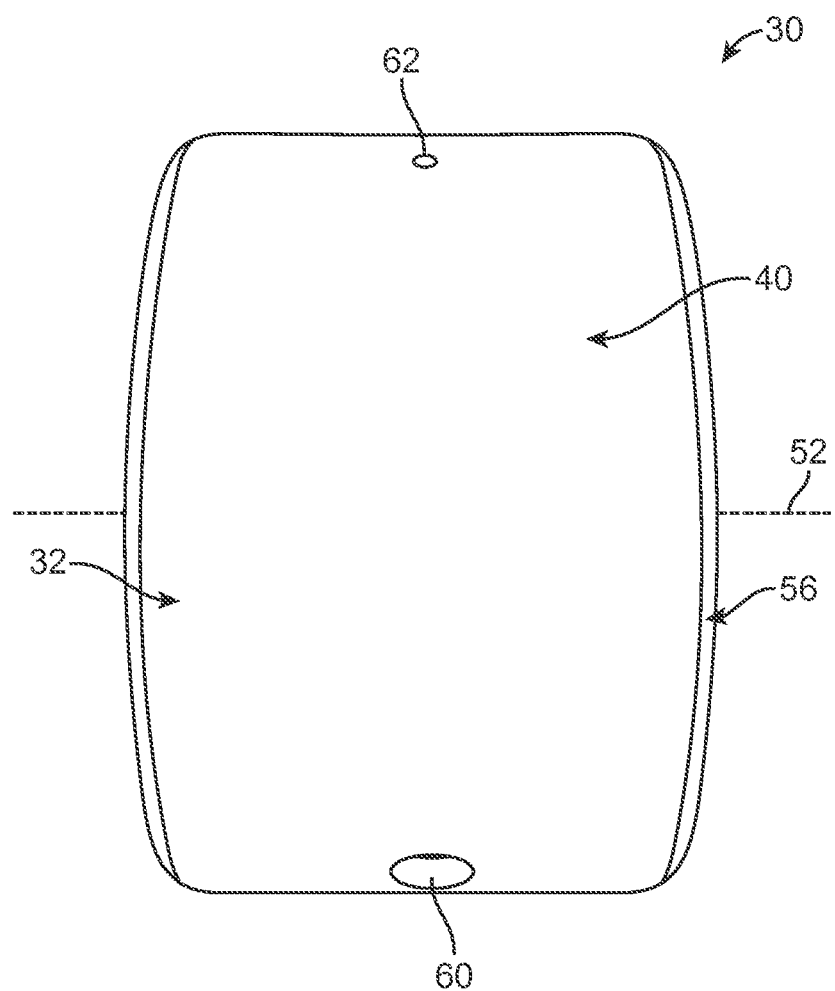
FIG. 6 is a top view of assessment tool.

FIG. 2 is a side view of an embodiment of a selectively attachable and removable visual and tactile assessment tool or clip 30 for use with mobile device 10. FIG. 3 is a perspective view of clip 30 and FIGS. 4-7 are alternative views of clip 30. Clip 30 is an elongate member having an outer surface 32 and an inner surface 34 forming a curvilinear shape. In some embodiments, clip 30 may comprise a single piece of material shaped as described above. In other embodiments, clip 30 may comprise several separate pieces as described above, each of which are affixed to one another.

Figure 7:
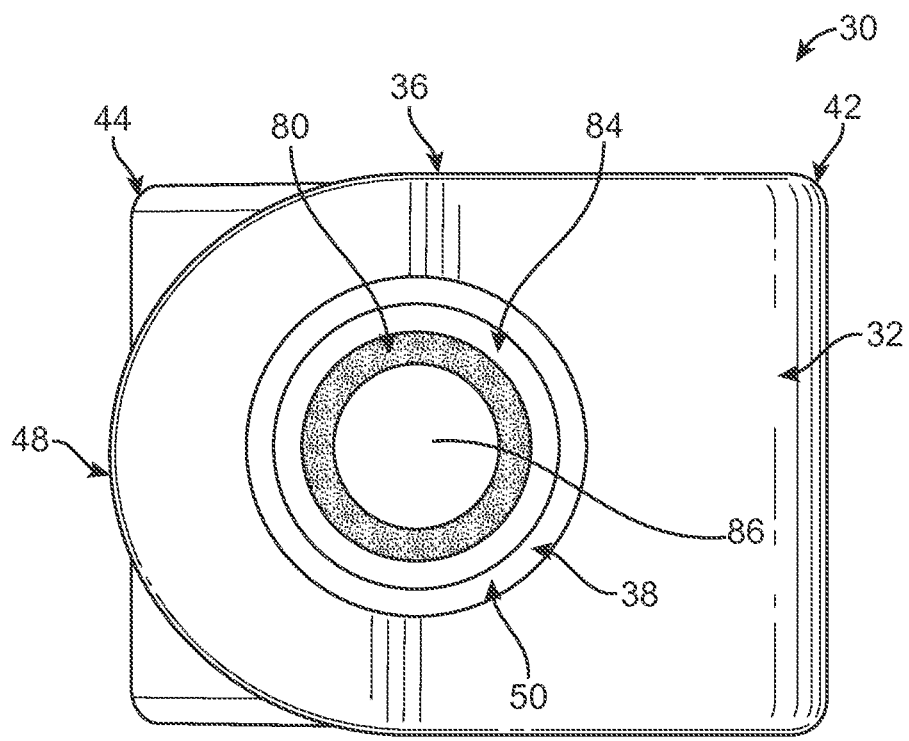
FIG. 7 is a bottom view of assessment tool.

Clip 30 has a first distal portion 36, a second distal portion 38 and a body portion 40 extending therebetween. First distal portion 36 forms a first bend 42 with respect to body portion 40 and second distal portion 38 forms a second bend 44 with respect to body portion 40. First distal portion 36 extends in a first direction 46 substantially parallel to a reference line A, which is horizontal in the FIG. 2. In an optional embodiment shown in FIG. 2, first distal portion 36 has a rounded tip 48 and first distal portion 36 forms an angle B with respect to a horizontal line A. In another optional embodiment as shown in FIGS. 2-3 and 7, first distal portion 36 has a finger opening 50 therethrough which allows a user to touch mobile device 10 during the process of attaching clip 30 to or removing clip 30 from mobile device 10 as will be further described herein.

Body portion 40 curves about a centerline 52 between first and second bends 42, 44 to form a curvilinear shape. In FIGS. 2-3, body portion 40 has a first section 54, a second section 56 and a third section 58. Merely for ease of description, clip 30 is shown in a position such that a first distal portion 36 may be considered as a bottom of clip 30 and a second section 56 may be considered as a top of clip 30. First bend 42 transitions into first section 54 which curves upwardly in a substantially vertical direction (with respect to horizontal line A). As first section 54 begins to transition into second section 56, body portion 40 curves further about centerline 52 to form an arch. In other embodiments, second section 56 could have an alternative shape about centerline such as a square, triangle about the centerline and is not limited to an arch shape.

Second section 56 has first and second openings 60, 62 each extending through body portion 40 from outer surface 32 to inner surface 34. First and second openings 60, 62 are on opposing sides of second section 56 and are in substantial alignment with one another. In an optional embodiment, body portion 40 could have a plurality of openings in a variety of corresponding alignment configurations (such as openings which are directly aligned with one another or openings which are in a criss-cross alignment) along the extent of body portion 40.

In another optional embodiment, a transparent tubular member 64 is disposed between first and second openings 60, 62 which help a user guide objects between first and second openings 60, 62. Additionally, first opening 60 can have a different size than second opening 62 as shown in FIGS. 3-6. Tubular member 64 can have varying internal diameter sizes such as a first diameter 66, corresponding with first opening 60 and a second diameter 68 corresponding with second opening 62, as shown in FIG. 2. The varying internal diameter sizes of tubular member 64 can simulate, for example, the constriction or stenosis of a patient's vessel lumen. In one embodiment, first diameter 66 is approximately the same size as a patient's vessel and second diameter 68 is smaller (for example, at least 10% smaller) than first diameter 66 to represent a stenosis of the vessel. For example, a medical device, such a balloon catheter is advanced from first diameter 66 where there is no stenosis to second diameter 68 where the stenosis exists, thereby simulating the look and feel of a stenosis within a patient's lumen. In an optional embodiment, tubular member 64 can have a contrasting color (not shown) extending along the length of first and/or second diameters 66, 68 wherein the contrasting color extends about at least a portion of the circumference of first and second diameters 66, 68. By having contrasting color in tubular member 64, a user can better see the advancement of catheter through tubular member 64. Although tubular member 64 is described in terms of inner diameters, tubular member 64 can have cross-sectional profiles with different shapes and sizes to accommodate a wide variety of objects passing therethrough, and tubular member 64 is not limited to receiving a medical device.

Second section 56 transitions into third section 58, which extends downward in a substantially vertical direction until third section 58 transitions into second bend 44. Second distal portion 38 extends from second bend 44 substantially parallel to horizontal line A in a second direction 70, which is opposite to first direction 46. As can be seen in FIG. 2, the curvature of body portion 40 results in second distal portion 38 being spaced apart from first distal portion 36. Spaced apart first and second distal portions 36, 38 define a retainer portion 72 for receiving mobile device 10 between first and second distal portions 36, 38.

The curvilinear shape of clip 30 and selection of materials for first distal portion 36, second distal portion 38 and body portion 40 are such that retainer portion 72 is variable to accommodate a plurality of sizes of mobile devices. In some embodiments, at least a portion first distal and second distal portions and body portion 36, 38, 40 can be made of a material (e.g., a polymer or a silicone) that is sufficiently elastic to permit a degree of bending or stretching in order to expand or widen retainer portion 72 to accommodate different sizes of mobile devices. When clip 30 is made of such a material, retainer portion 72 may be temporarily widened while sliding clip 30 onto mobile device, but at least body portion 40 remains sufficiently stiff, rigid, or resilient to urge at least one of the first and second distal portions 36, 38 to return to its original position. In this manner, first and second distal portions 36, 38 exert a gripping force against a portion of mobile device 10. The material of clip 30, or some portion thereof (e.g., inner surface 32 of first distal portion 36 or outer surface 32 of second distal portion 38), can also be textured, tacky or otherwise somewhat slide resistant to enhance the gripping of the retainer portion to mobile device.

In one embodiment, first and second distal portions 36, 38 are more stiff or rigid than body portion 40. In this way, body portion 40 can sufficiently flex but yet is resilient enough to maintain the original shape of clip 30. Whereas, first and second distal portions 36, 38 can maintain a more rigid configuration and are moved out of their positions (relative to each other) by the flexing of body portion 40. First and second distal portion 36, 38 having more rigidity than body portion 40 would provide are more advantageous contact or grasping force being applied to mobile device 10. As described above, first distal portion 36 can form an angle B with respect to horizontal line A. In this embodiment, first distal portion 36 has more flexing capability than second distal portion 38 by being able to flex in at least a plurality of ranges with angle B.

Second distal portion 38 has an optical system 80, as shown in FIGS. 2-3 and 7. Second distal portion 38 has sidewalls 82 defining a second distal portion opening 84 extending through second distal portion 38, wherein opening 84 is sized to receive optical system 80 therein. FIG. 7 shows second distal portion opening 84 and optical system 80 in substantial alignment with finger opening 50 of first distal portion 36. Optical system 80 may include one or more optical components, such as a lens 86 (or lenses, e.g., zoom lenses, polarizer lenses, lens color filters, fish-eye lenses, wide-angle lenses, anti-reflection lenses, anti-glare lenses, telephoto lenses, microscopic lenses or magnification lenses) for use with the onboard cameras 24, 26 of mobile device 10. Lens 86 can also comprise coatings or other features to increase scratch resistance, diminish glare or reflection, or even decrease or filter light transmitted through lens.

In an optional embodiment, a light source (not shown) is disposed on inner surface 32 of clip 30 to illuminate tubular member 64. The light is powered by a battery disposed within clip 30 or powered by an external power supply connection on clip 30. The light can be turned on by either a manual button or a trigger (not shown) in retainer portion which is activated when clip 30 is attached to mobile device 10. In another embodiment, a light source is disposed on second distal portion 38 about the periphery of lens 86 to provide illumination from beneath tubular member 64.

In some embodiments, the optical components of optical system 80 may be either releasably coupled to or integrally formed with second distal portion 38. In some embodiments, multiple lenses can be configured to provide a variable optical magnification (e.g., a zoom feature) by permitting manipulation of the distance between the lenses, such as with a lever or rotating actuator (e.g., a thumb wheel). Sidewalls 82 of second distal portion 38 can comprise a connection portion (not shown), such as an internal or external threaded portion. The threaded portion can facilitate removably attaching multiple optical components, such as an additional lens or lens cap, to second distal portion 38.

In some embodiments, optical system 80 may attach to second distal portion 38 such that optical system 80 or lens 86 may be adjusted with respect to a mobile device (e.g., azimuthally, along the optical component's vertical axis, along the optical component's horizontal axis, or a combination of these adjustments, etc.). In some embodiments, optical system 80 or lens 86 may also be coupled to second distal portion 38 in such a way that the optical system 80 or lens 86 may be tilted (e.g., coupled to second distal portion 38 by a ball and socket joint). The ability to adjust optical system 80 with respect to mobile device can be advantageous in addressing manufacturing differences or tolerances in the location and/or alignment of the onboard camera lenses in some mobile devices, or alternatively advantageous in addressing a variety of differently shaped objects passing between first and second openings 60, 62.

Figure 8:
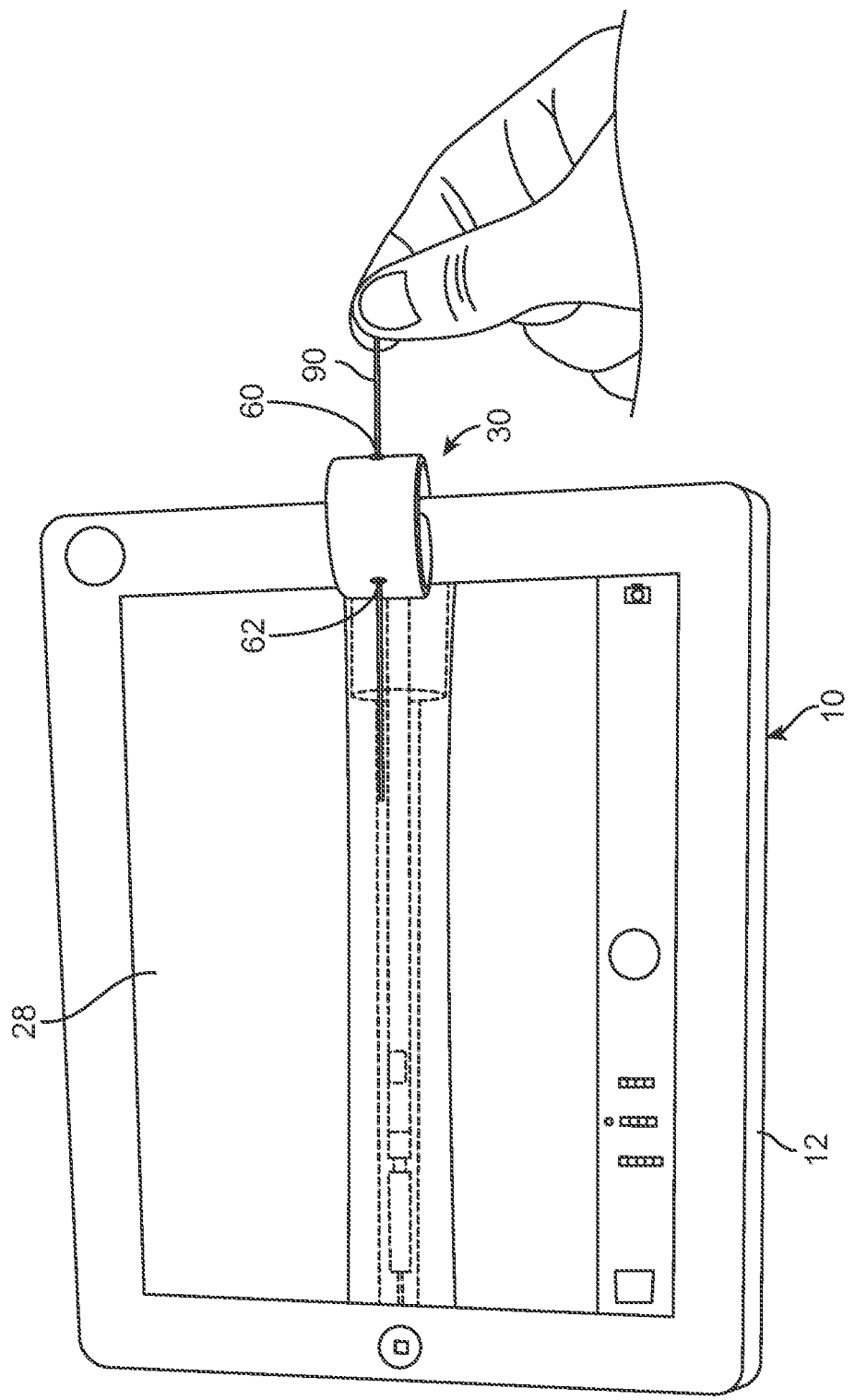
FIG. 8 is a perspective view of a user tracking an exemplary catheter with assessment tool while mobile device displays the catheter of the screen.

Clip 30 is removably coupled to mobile device 10 by retainer portion 72 receiving mobile device 10 between first and second distal portions 36, 38 (as shown in FIG. 8) such that inner surface 32 of first distal portion 36 contacts front face 12 of mobile device 10 and outer surface 32 of second distal portion 38 contacts rear face 14 of mobile device 10. Optical system 80 is aligned substantially co-axial with finger opening 50 of first distal portion 36, as shown in FIG. 7. In this way, clip 30 enables repeatable, precise placement of optical system 80 over onboard cameras 24, 26 in a single attachment motion without requiring the user to adjust the location or structure of the optical system during attachment.

Once clip 30 is attached to mobile device, an object, such as a balloon catheter 90, is inserted through first opening 60 of body portion 40, as shown in FIG. 8. Catheter 90 slides without restriction through first diameter 66 of tubular member 64 until catheter 90 reaches second diameter 68 of tubular member 64. At this point, the user must exert more pressure to advance catheter 90 through second diameter 68 and out second opening 62 of body portion 40. During the advancement of catheter 90 through tubular member 64, the video image received through onboard camera 24 is displayed on screen 28. In one embodiment, optical system 80 acts as a magnifying lens to enlarge the size of the catheter 90 displayed on screen 28. Accordingly, the user can see in detail how catheter 90 passes through second diameter 68 while at the same time assesses the tactile feel of catheter 90 thereby simulating passing the same or similar catheter through a stenosis of a vessel lumen. In an optional embodiment, a software application or "app" can reside on mobile device 10 to store video or images of catheter 90 passing through tubular member 64 for further analysis or processing.

In other embodiments, clip 30 does not have a tubular member 64. In this embodiment, first and second openings 60, 62 could be any size or shape to receive a variety of different objects for assessment or analysis by optical system 80. For example, a slide or other sample holder (not shown) having particles or other biological elements disposed thereon, could be advanced through first and second openings 60, 62. When the particles on the slide are in alignment with optical system 80, the onboard cameras 24, 26 receive an image of the particle details, which are in turn displayed onto screen 28.

Figure 9:
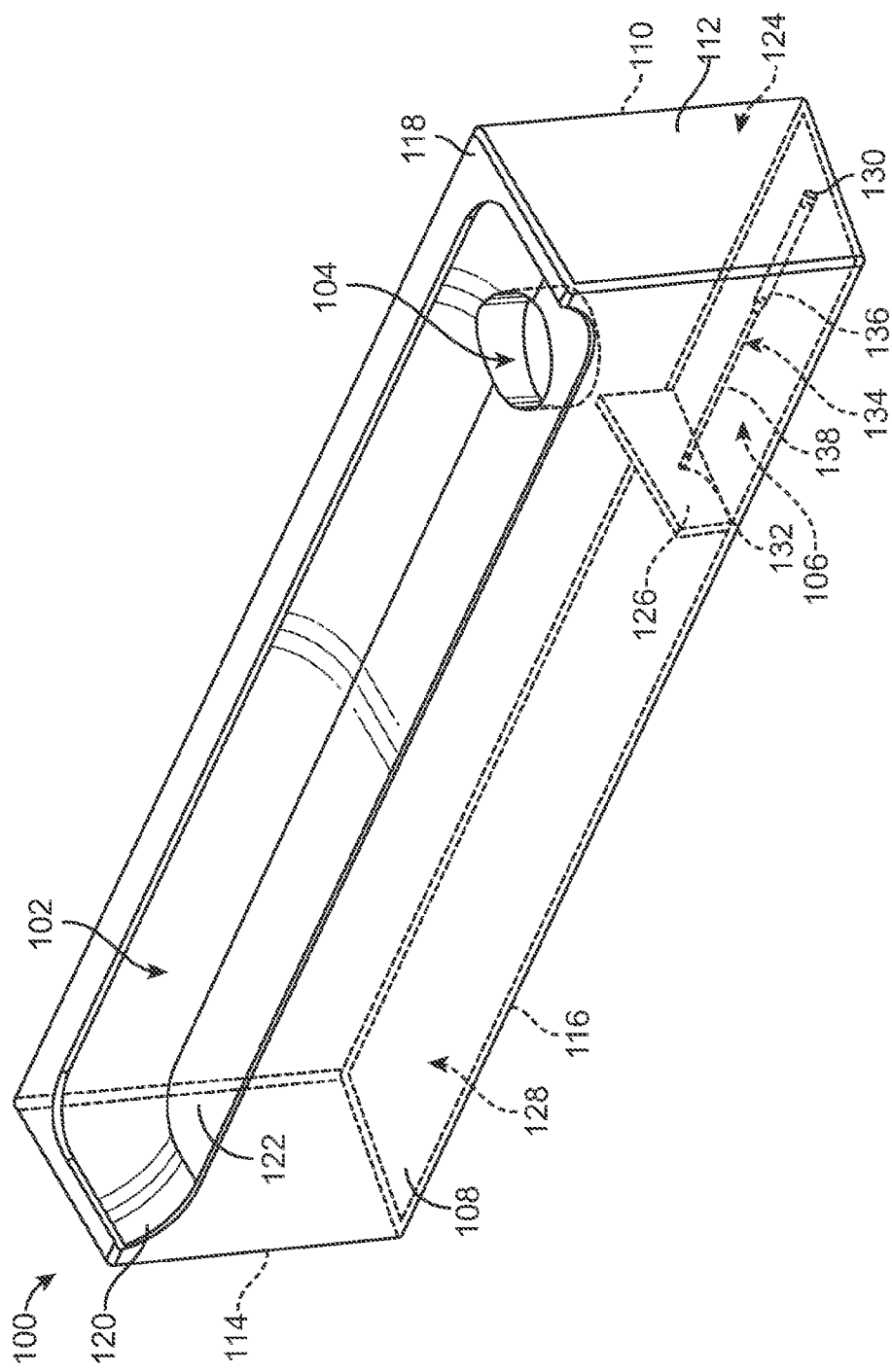
FIG. 9 is a perspective view of an alternative embodiment of assessment tool.

FIG. 9 is a perspective view of another embodiment of a selectively attachable and removable visual and tactile assessment tool or support member 100 for use with mobile device 10. Support member 100 has a receiving portion 102, an optical system 104 disposed within receiving portion 102 and an analysis portion 106. (Optical system 104 and analysis portion 106 are disposed within support member 100 and are shown in phantom lines to better understand this embodiment of the Invention.) Although support member 100 is shown in an elongate and rectangular shape, other shapes and sizes are within the scope of support member 100. Support member 100 has a front surface 108, rear surface 110, first and second side surfaces 112, 114, a bottom surface 116 and a top surface 118.

Receiving portion 102 is formed into top surface 118 and intersects with front surface 108. Receiving portion 102 is shaped to accommodate a wide variety of shapes of mobile devices by having a concave shape. As shown in FIG. 9, receiving portion 102 has curved sidewalls 120 which converge on a substantially planar surface 122. In one embodiment, planar surface 122 is substantially parallel with bottom surface 116. In another embodiment, planar surface 122 is angled with respect to bottom surface 116.

FIG. 9 shows optical system 104 recessed within receiving portion 102 of support member 100, which allows mobile device 10 to lay flat on planar surface 122. Optical system 104 is positioned adjacent to one side of support member 100 in order to be in alignment with onboard camera 26 which is located on rear face 14 along top edge 16 and adjacent a corner of rear face 14. Thus, optical system 104 is disposed above and in visual communication with analysis portion 106 in order to capture images or video of objects disposed within analysis portion 106. However, optical system 104 can be disposed anywhere along the extent of receiving portion 102 of support member 100 to accommodate onboard cameras which may be positioned anywhere along top edge 16 on front face 12 of mobile device 10. Accordingly, analysis portion 106 would be disposed beneath optical system 104 depending on where optical system 104 is positioned along the extent of receiving portion 102. Optical system 104 has at least the same features and characteristics as optical system 80 described herein.

Analysis portion 106 has a first cavity 124 defined by front, rear, bottom and first side surfaces 108, 110, 112, 116 and an internal side wall 126. Support member 100 has a second cavity 128 disposed beneath receiving portion 102 and is defined by front, rear, bottom and second side surfaces 108, 110, 114, 116 and internal side wall 126. Analysis portion 106 has a first opening 130 through first side surface 112 and a second opening 132 through internal side wall 126. In an optional embodiment, analysis portion could have a plurality of openings in corresponding alignment configurations (such as openings which are directly aligned with one another or openings which are in a criss-cross alignment) in at least front, rear, bottom, first side and second side surfaces 108, 110, 112, 114, 116, 118 and internal side wall 126. First and second openings 130, 132 are on opposing sides of first cavity 124 and in substantial alignment with one another. In an optional embodiment, a transparent tubular member 134 is disposed between first and second openings 130, 132 which helps a user guide objects through both first and second openings 130, 132. First opening 130 can have a different size than second opening 132. Additionally, tubular member 134 can have varying inner diameter sizes such as a first diameter 136, corresponding with first opening 130 and a second diameter 138 corresponding with second opening 132, as shown in FIG. 9. The varying inner diameter sizes of tubular member 134 can simulate, for example, the constriction or stenosis of a patient's vessel lumen. In one embodiment, first inner diameter 136 is approximately the same size as a patient's vessel and second inner diameter 138 is smaller (for example, at least 10% smaller) than first diameter 136 to represent stenosis of the vessel. For example, a medical device, such a balloon catheter is advanced from first diameter 136 where there is no stenosis to second diameter 138 where the stenosis exists, thereby simulating the look and feel of a stenosis within a patient's vessel. In an optional embodiment, tubular member 134 can have a contrasting color (not shown) extending along the length of first and/or second diameters 136, 138 wherein the contrasting color extends about at least a portion of the circumference of first and second diameters 136, 138. By having contrasting color in tubular member 134, a user can better see the advancement of catheter through tubular member 134. Although tubular member 134 is described in terms of inner diameters, tubular member 134 can have different shapes and cross-sectional profiles to accommodate a wide variety of objects passing therethrough, and tubular member 134 is not limited to receiving a medical device.

In an optional embodiment, a light source (not shown) is disposed within first cavity 124 to illuminate tubular member 134. The light is powered by a battery disposed within support member 100 or powered by an external power supply connection on support member 100. The light can be turned on by either a manual button or a trigger in receiving portion 102 that is activated when mobile device 10 is received within receiving portion 102.

Figure 10:
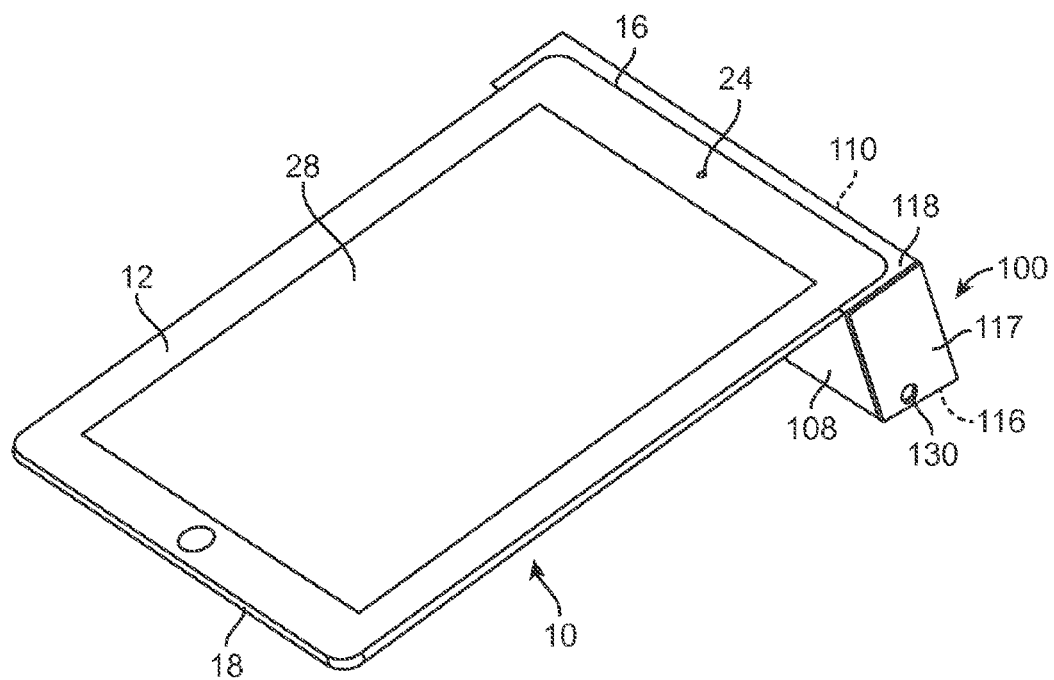
FIG. 10 is a perspective view of the assessment tool of FIG. 9 receiving an exemplary mobile device.

Mobile device is removably receivable within receiving portion 102 of support member 100 as shown in FIG. 10. As described above, support member 100 can have a plurality of shapes so that mobile device can be positioned in a plurality of angles (with respect to a horizontal surface) to improve viewing of the screen by the user. In addition, as described above, planar surface 122 can be formed in a plurality of angles (with respect to bottom surface) to improve viewing of screen 28 by the user. Optical system 104 is aligned such that it is substantially co-axial with onboard camera 26. In this way, support member 100 enables repeatable, precise placement of optical system 104 over onboard camera 26 in a single attachment motion without requiring the user to adjust the location or structure of the optical system 104 during attachment.

Once mobile device 10 is received by support member 100, an object, such as a balloon catheter, is inserted through first opening 130 of first side surface 112. Catheter slides without restriction through first inner diameter 136 of tubular member 134 until catheter reaches second inner diameter 138 of tubular member 134. At this point, the user must exert more pressure to advance catheter through second diameter 138 and out second opening 132. Once catheter has passed second opening 132, the portion of the catheter distal to second opening 132 is disposed within second cavity 128 of support member 100. Second cavity 128 allows enough space for the user to advance and retract the longitudinal extent of the catheter through the analysis portion 106.

During the advancement of catheter through tubular member 134, onboard camera 26 is receiving an image of the progress and displaying the image on screen 28 of mobile device 10, as shown in FIG. 10. In one embodiment, optical system 104 acts as a magnifying lens to enlarge the size of the catheter which is displayed onto screen 28. Accordingly, the user can see in detail how catheter passes through second diameter while at the same time assess the tactile feel of catheter thereby simulating passing the same catheter through a stenosis of a vessel lumen.

In other embodiments, analysis portion 106 does not have a tubular member 134. In this embodiment, first and second openings 130, 132 could be any size or shape to receive a variety of different objects for assessment or analysis by optical system 104. For example, a slide or other sample holder (not shown) having particles or other biological elements disposed thereon, could be advanced through first and second openings 130, 132. When the particles on the slide are in alignment with optical system 104, onboard camera 26 receives an image of the particle details, which are in turn displayed onto screen 28.

The detailed description is merely exemplary in nature and is not intended to limit the invention or the application and uses of the invention. Although the description of the invention is in the context of treatment of blood vessels such as the coronary arteries, the invention may also be used in any other body passageways where it is deemed useful such as but not limited to peripheral arteries, carotid arteries, renal arteries, and/or venous applications. Furthermore, there is no intention to be bound by any expressed or implied theory presented in the preceding technical field, background, brief summary or the detailed description.

While various embodiments according to the present invention have been described above, it should be understood that they have been presented by way of illustration and example only, and not limitation. It will be apparent to persons skilled in the relevant art that various changes in form and detail can be made therein without departing from the scope of the invention. Thus, the breadth and scope of the present invention should not be limited by any of the above-described exemplary embodiments. It will also be understood that each feature of each embodiment discussed herein, and of each reference cited herein, can be used in combination with the features of any other embodiment.

What is claimed is:

1. A tool comprising:
   an elongate body portion having first and second distal portions, wherein the body portion has a curvilinear shape between the first and second distal portions, and the first and second distal portions extend in substantially parallel directions in a spaced apart configuration to receive a mobile device having a camera;
   a first opening and a second opening through the body portion, wherein the first and second openings are in substantial alignment with one another such that an object may pass through at least one of first or second openings; and
   an optical system disposed on the second distal portion and spaced from the first and second openings, wherein the optical system is positionable over the camera of the mobile device and is configured to magnify an area between the first and second openings.

2. The tool of claim 1, further comprising a transparent tubular member disposed in the area between the first and second openings.

3. The tool of claim 2, wherein the tubular member has varying inner diameters.

4. The tool of claim 2, wherein the tubular member has contrasting color extending along a length of the tubular member about at least a portion of a circumference of an inner diameter of the tubular member.

5. The tool of claim 1, wherein the first distal portion extends in a first direction and the second distal portion extends in a second direction which is opposite to the first direction.

6. The tool of claim 1, wherein at least one of the body portion, the first distal portion, or the second distal portion is sufficiently elastic to permit bending in order to expand the distance between the first and second distal portions.

7. The tool of claim 6, wherein the body portion is sufficiently resilient to urge at least one of the first or second distal portions to return to the original configuration.

8. The tool of claim 1, wherein the optical system includes a magnifying lens to enlarge an image of the object passing through at least one of the first or second openings.

9. The tool of claim 1, further comprising a light disposed on at least one of the body portion, the first distal portion, or the second distal portion to illuminate the object passing through at least one of the first or second openings.

10. A support member comprising:
    a receiving portion formed to receive a portion of a mobile device having a camera;
    an optical system disposed within the receiving portion such that the optical system is aligned with the camera of the mobile device when the mobile device is received within the receiving portion; and
    an analysis portion disposed within support member and beneath the optical system, the analysis portion having at least first and second openings, wherein the first and second openings are in substantial alignment with one another such that an object may pass through at least one of first or second openings, wherein the optical system is configured to magnify an area between the first and second openings.

11. The support member of claim 10, wherein the receiving portion has a concave shape formed into a top surface of the support member.

12. The support member of claim 10, wherein the optical system is recessed within receiving portion allowing the mobile device to lay flat within the receiving portion.

13. The support member of claim 10, wherein the optical system is in visual communication with the analysis portion.

14. The support member of claim 10, wherein the optical system includes a magnifying lens to enlarge an image of the object passing through at least one of the first or second openings.

15. The support member of claim 10, further comprising a transparent tubular member disposed between the first and second openings.

16. The support member of claim 15, wherein the tubular member has varying inner diameters.

17. The support member of claim 15, wherein the tubular member has contrasting color extending along a length of the tubular member about at least a portion of a circumference of an inner diameter of the tubular member.

18. The support member of claim 10, further comprising a light disposed adjacent or within the analysis portion to illuminate the object passing through at least one of the first or second openings.

19. The support member of claim 10, wherein the first opening is through a side wall of the support member, and the second opening is through an internal side wall.

20. A tool comprising:
- an elongate body portion having first and second distal portions, wherein the body portion has a curvilinear shape between the first and second distal portions, the first and second distal portions extend in substantially parallel directions in a spaced apart configuration to receive a mobile device having a camera;
- a first opening and a second opening through the body portion, wherein the first and second openings are in substantial alignment with one another such that an object may pass through at least one of first or second openings;
- a transparent tubular member disposed between the first and second openings; and
- an optical system disposed on the second distal portion, wherein the optical system is positionable over the camera of the mobile device.

* * * * *